(12) United States Patent
Serhan

(10) Patent No.: US 9,155,600 B2
(45) Date of Patent: Oct. 13, 2015

(54) PROTECTIVE DENTAL POST SYSTEM FOR TEETH WITH EXCESSIVE DENTAL MATERIAL LOSS

(71) Applicant: Akman Serhan, Konya (TR)

(72) Inventor: Akman Serhan, Konya (TR)

( * ) Notice: Subject to any disclaimer, the term of this patent is extended or adjusted under 35 U.S.C. 154(b) by 0 days.

(21) Appl. No.: 14/348,895

(22) PCT Filed: Nov. 6, 2012

(86) PCT No.: PCT/TR2012/000193
§ 371 (c)(1),
(2) Date: Apr. 1, 2014

(87) PCT Pub. No.: WO2013/100868
PCT Pub. Date: Jul. 4, 2013

(65) Prior Publication Data
US 2014/0248586 A1    Sep. 4, 2014

(30) Foreign Application Priority Data
Dec. 27, 2011    (TR) ................ a 2011/13007

(51) Int. Cl.
*A61C 13/30*    (2006.01)

(52) U.S. Cl.
CPC .................... *A61C 13/30* (2013.01)

(58) Field of Classification Search
CPC ............... A61C 13/30; A61C 5/005
USPC ................................ 433/219–225
See application file for complete search history.

(56) References Cited

U.S. PATENT DOCUMENTS

| | | | | |
|---|---|---|---|---|
| 3,831,281 | A * | 8/1974 | Edelman | 433/225 |
| 4,348,183 | A | 9/1982 | Weissman | |
| 4,616,999 | A * | 10/1986 | Weissman | 433/225 |
| 5,775,910 | A * | 7/1998 | Orrico | 433/221 |
| 2003/0235805 | A1 | 12/2003 | Lax | |

FOREIGN PATENT DOCUMENTS

DE    3806891 A1    7/1988

* cited by examiner

*Primary Examiner* — Edward Moran
(74) *Attorney, Agent, or Firm* — Gokalp Bayramoglu

(57) ABSTRACT

The invention is about the dental post system designed to protect the dental tissues left and is aimed to use for the treatment of teeth with excessive dental material loss in the fields of endodontic, prosthetic dental treatment and pedodontics.

3 Claims, 5 Drawing Sheets

PROTECTIVE DENTAL POST SYSTEM FOR TEETH WITH EXCESSIVE DENTAL MATERIAL LOSS

TECHNICAL FIELD

Figure 1:
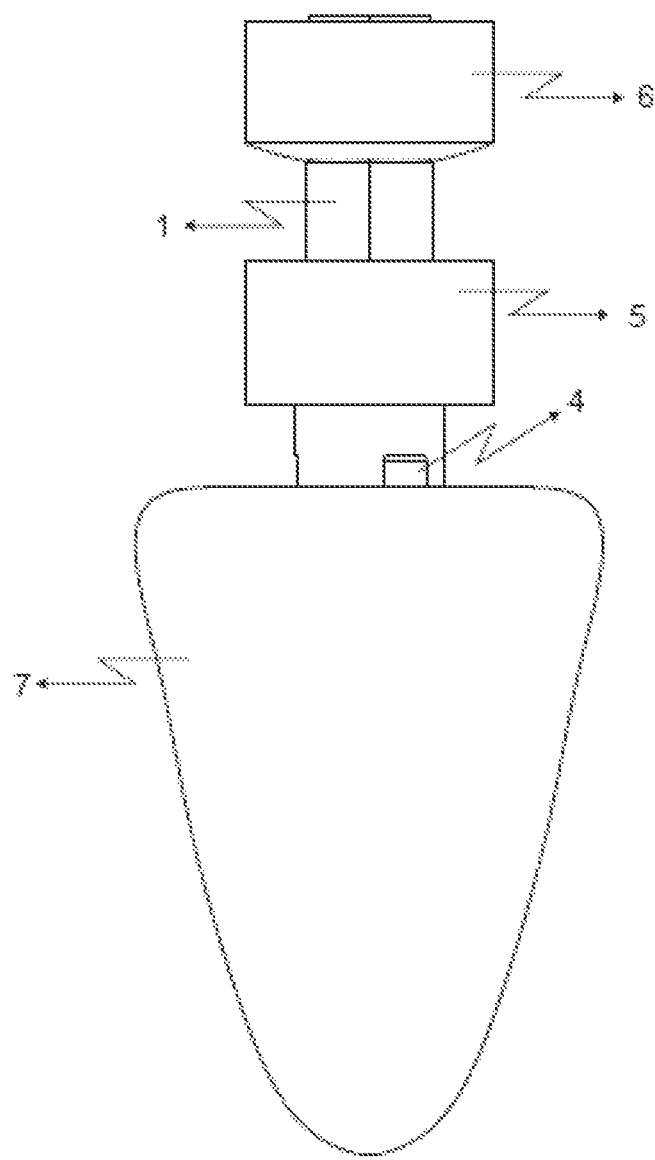

The invention is about the dental post system designed to protect the dental tissues left and is aimed to use for the treatment of teeth underwent excessive dental material loss in the fields of endodontic, prosthetic dental treatment and pedodontics.

PRIOR ART

The teeth, underwent considerable amount of coronal and radicular tissue loss caused by decay, root canal therapy, erosion, abrasion or trauma, need restoration as a functioning part of dental arc. If the restorated tooth is to act as a backer tooth in the removable or fixed denture, the expectations are greater. The essential part of these type restorations is dental post. In dentistry, the treatment of the teeth exposed to excessive object loss has been achieved commonly by using dental posts for many years.

Dental post should create retention and resistance to core material and/or restoration to mend the lost dental tissues. Amalgam, composite resin or glass ionomer are widely used core materials. Nowadays, composite resin restorations together with dental post are commonly applied to strengthen the teeth without crown and exposed to excessive material loss. Crowns distribute the power onto the core equally in the teeth underwent excessive material loss and treated endodotically.

Angular dental posts design is in harmony with the root and canal structure of the natural tooth and less preparation is performed for the cavity in the tooth to be placed. Although parallel dental posts are usually retentive, more preparation is required for the cavity in the tooth to be placed. When the post surface is grooved or rough, it furnishes additional mechanic attachment and increases retention considerably.

The materials used in dental posts must be stress-proof to functions, resistant to corrosion and biocompatible. Metals (stainless steel, nickel-chrome, titanium), ceramic, zirconium, systems reinforced with fibers are widely used as dental post materials.

The cements widely used to adhere dental posts are zinc phosphate, polycarboxylate, ethylcyanoacrylate, composite resin, glass ionomer and resin-modified glass ionomer cement. Cementation has an important role in connecting tooth to dental post, distributing stress and boosting retention. The stress in the root canal increases as a result of the hydrostatic pressure during cementation. The pressure varies according to the viscosity of the cement. Stress can be reduced through cement escape way. Thus, hydrostatic pressure decreases.

The teeth underwent endodontic therapy are more fragile than the teeth with live pulp. The fractures occurred in the restoration or core material caused by the pressure in the mouth can move across the dental tissues left. These fractures usually occur in the oblique or vertical shape. The most important cause of the loss of the teeth underwent excessive material loss in dentistry is the oblique or vertical root fractures caused by the pressure that occurs in the mouth in time after restorative therapy.

The dental posts on the market today are structures rested upon the interior canal and looks like a screw to which core structure is connected. This dental post design creates a wedge effect on the root and the fracture line occurred in the core or restoration causes an oblique or vertical fracture in the root. When the fracture line or crack occurred in the core structure or restoration leads to dental post in time, dental post moves across core interface and dental post-dental tissues interface and causes an oblique or vertical fracture in the dental tissues left (root). The repetition of the therapy may not be possible and the rest of the tooth may be lost because of his complication. All of the dental posts on the market today forward the fracture line into the core or root. The use of dental post for the treatment of the teeth underwent excessive material loss is considered as a last resort and patients are told that tooth must be pulled out in likely fracture complications.

BRIEF ABSTRACT OF THE INVENTION

Invention; the dental post system, made up of a washer with flat underside (5.1), and concave upside (5.2), and on it a coronal washer (6) with convex underside (6.1) and concave upside (6.2), prevents the fracture line to extend into the root and to cause a fracture in the root in the col region of the tooth underwent excessive material loss. Moreover, the apical end of the dental post has a flat surface and a base is prepared in the root for this flat surface. This flat surface at the apical end of the dental post is located into the prepared base. Thus, the stress transferred via the dental post is conveyed to the root through his base. It does not create a wedge effect.

LIST OF FIGURES

Figure 2:
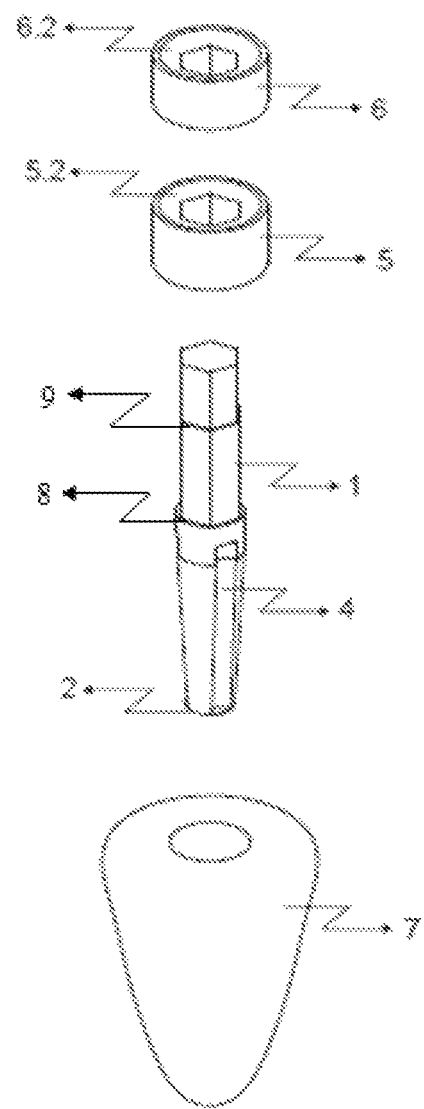
Figure 3:
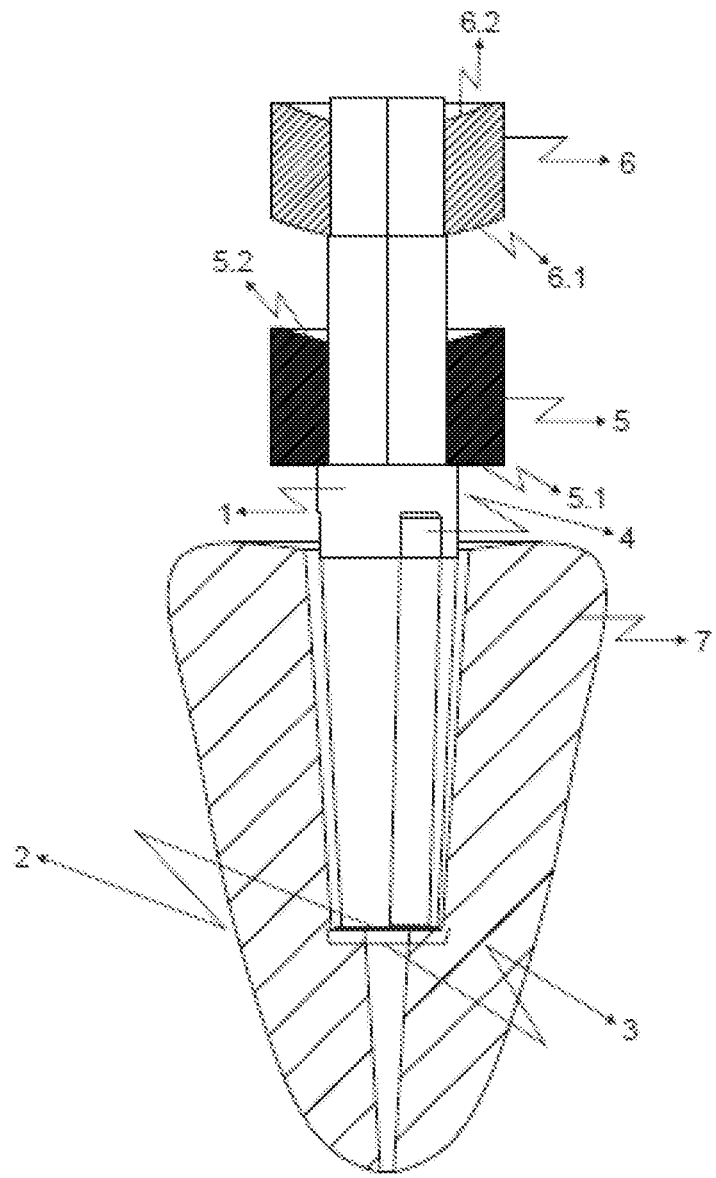
Figure 4:
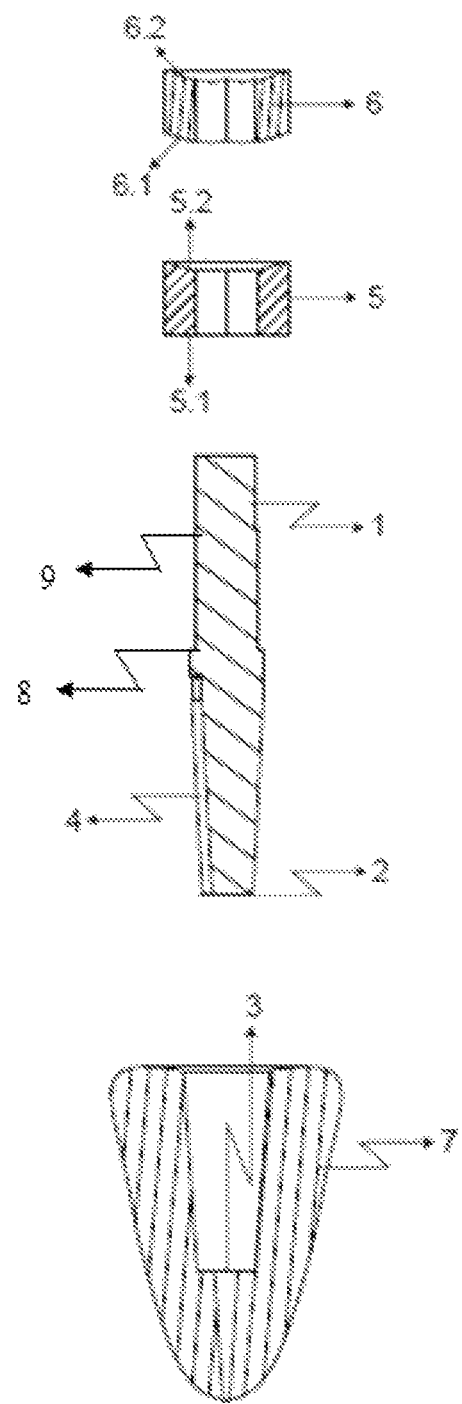
Figures 5A, 5B:
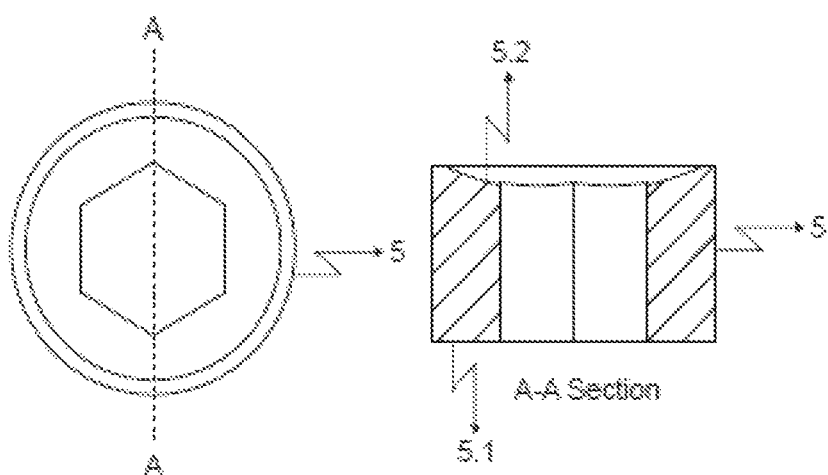
Figures 6A, 6B:
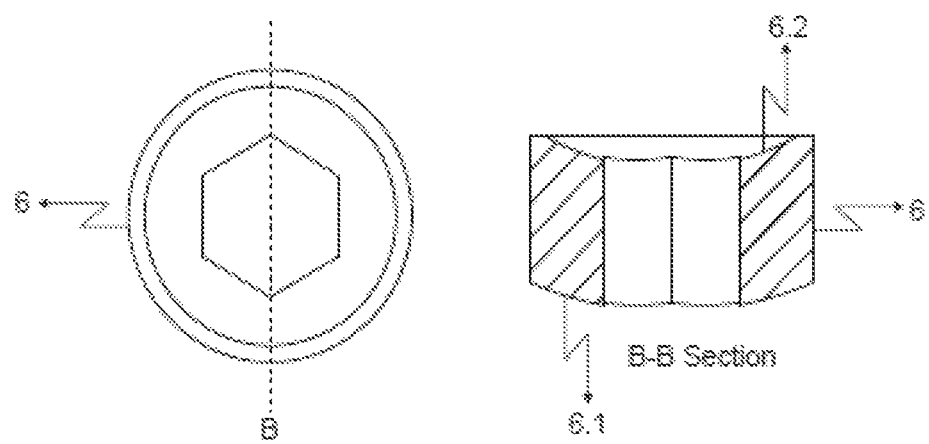

FIG. 1. A General Mounted Outlook
FIG. 2. Dismantled Outlook
FIG. 3. Cutaway View
FIG. 4. Disassembled Cutaway View
FIG. 5. a col Washer Plan View FIG. 5b. Col Washer A-A Section View
FIG. 6. a Coronal Washer Plan View FIG. 6b. Coronal Washer B-B Section View

DESCRIPTION OF THE REFERENCE NUMERALS

1. Dental Post Trunk
2. Dental Post Bottom
3. Root Base
4. Cement Escape way
5. Col Washer
    5.1. Underside Flat Surface
    5.2. Upside Concave Surface
6. Coronal Washer
    6.1. Underside Convex Surface
    6.2. Upside Concave Surface
7. Tooth Root
8. Col Washer Base
9. Coronal Washer Base

DETAILED DESCRIPTION OF THE INVENTION

Invention; the dental post is made up of the parts of dental post trunk (1), dental post bottom (2), root base (3), cement escape way (4), Col washer (5) with flat surfaced (5.1) underside and concave surfaced (5.2) upside, coronal washer (6) with convex surfaced (6.1) underside and concave surfaced (6.2) upside and tooth root (7).

A proper cavity to locate the dental post trunk is prepared in the root of the tooth underwent excessive material loss. A root base (3) matching with the diameter of the tip of the dental post trunk (1) in the root is prepared at the bottom of this cavity. The trunk dental post (1) is cemented into the cavity prepared in the root. Surplus cement can pass out through the escape way (4) during cementation.

Escape ways inside the tooth are extended outside the tooth tissues to enable the cement to pass out with ease. The stresses conveyed via dental post trunk (1) are transferred vertically into the root through the root base (3). Wedge effect and hydrostatic pressure do not occur on the root during and after cementation. The dental post trunk (1) is designed so that its diameter (angled) narrows towards the passive root and has escape ways (4). The dental post system made up of a col washer (5) in the col region, with flat underside (5.1), and concave upside (5.2), and on it a coronal washer (6) with convex underside (6.1) and concave upside (6.2), prevents the fracture line to extend into the root and to cause a fracture in the root.

If the fracture lines occurred, in time, in the restoration and core structure affect coronal washer (6) after the protective dental post application is performed in the cases with teeth underwent excessive material loss, the concave upside (6.2) of coronal washer (6) shifts the direction of a fracture line in the way that it does not damage the remaining tooth tissues. Similarly, the direction of a fracture line occurred in the lower parts is shifted with the concave upside (5.2) of col washer (5) so that it does not damage tooth tissues.

The section of the place where dental post trunk (1) locate on the col washer is hexagonal shaped so that col washer (5) can stay in the dental post trunk (1) without rotating, and it provides a space between the tooth tissue and a col washer base (8) where the col washer will rest. The counterpart of this hexagon is also prepared in the inner surface of the col washer (5). A hexagon as in the cole washer (5) is applied so that coronal washer (6) cannot rotate on the trunk dental post (1). A coronal washer base (9) on which coronal washer can rest is formed on the dental post trunk to keep the distance between the col (5) and coronal washer (6).

The repair of the fractures occurred in restoration and core structure is made easier thanks to the system described. In a possible fracture state, the restoration on the coronal washer (6) and renewal of core structure can be achieved easily while the col washer (5) and its connection with tooth tissues are not damaged at all.

The invention claimed is:

1. A dental post, comprising:
   a dental post trunk (1);
   wherein the dental post trunk (1) further comprises a flat surfaced dental post bottom (2) which is capable of vertically conveying a stress from the dental post trunk (1) to a root base (3), and a coronal end opposite the post bottom;
   a coronal washer (6) having a convex underside (6.1) facing the post bottom and a concave upside (6.2) facing the coronal end;
   a col washer (5) comprising a completely flat underside (5.1) facing the post bottom and a concave upside (5.2) facing the coronal end;
   wherein both the col washer (5) and the coronal washer (6) are capable of shifting the direction of a fracture line in the way that it does not damage a remaining tooth tissues; and
   wherein the coronal washer (6) and col washer (5) are completely separated from each other and any of the remaining tooth tissues and are removably located on a coronal washer base (8) and a col washer base (9), respectively, formed on an upper part of the post trunk.

2. The dental post according to claim 1, wherein the upper part of the dental post trunk (1) has a hexagonal shape.

3. The dental post according to claim 2, wherein an inner surface of the col washer (5) has a hexagonal shape matching with the dental post trunk and (1), wherein an inner surface of the coronal washer (6) has a hexagonal shape matching with the dental post trunk (1).

* * * * *